United States Patent [19]
Noda

[11] Patent Number: 5,849,854
[45] Date of Patent: Dec. 15, 1998

[54] PROCESS FOR RECOVERING POLYHYDROXYALKANOTES USING AIR CLASSIFICATION

[75] Inventor: Isao Noda, Fairfield, Ohio

[73] Assignee: The Proctor & Gamble Company, Cincinnati, Ohio

[21] Appl. No.: 549,638

[22] Filed: Oct. 26, 1995

Related U.S. Application Data

[63] Continuation-in-part of Ser. No. 251,829, Jun. 1, 1994, abandoned.

[51] Int. Cl.$^6$ ...................................... C08G 83/00
[52] U.S. Cl. ............................ 528/1; 530/370; 530/372; 530/377; 530/376; 530/378; 530/412; 530/427; 528/1; 528/2; 426/425; 426/431; 560/1
[58] Field of Search ...................................... 530/370, 372, 530/377, 376, 378, 412, 427; 528/1, 2; 426/425, 431; 560/1

[56] References Cited

U.S. PATENT DOCUMENTS

| | | | |
|---|---|---|---|
| 3,036,959 | 5/1962 | Baptist et al. | 195/47 |
| 3,275,610 | 9/1966 | Mobil Oil Corporation | 530/80 |
| 3,828,017 | 8/1974 | Finley et al. | 530/375 |
| 3,869,438 | 3/1975 | Finley et al. | 530/377 |
| 3,895,003 | 7/1975 | Swain et al. | 530/377 |
| 4,146,534 | 3/1979 | Armstrong | 530/377 |
| 4,174,314 | 11/1979 | Garrison | 530/377 |
| 4,174,315 | 11/1979 | Garrison et al. | 530/377 |
| 4,175,075 | 11/1979 | Garrison et al. | 530/377 |
| 4,215,040 | 7/1980 | Hager | 530/378 |
| 5,110,980 | 5/1992 | Ramsay et al. | 560/185 |

FOREIGN PATENT DOCUMENTS

| | | |
|---|---|---|
| 0 015 123 | 9/1980 | European Pat. Off. . |
| 0 046 355 | 2/1982 | European Pat. Off. . |
| 0 533 144 A2 | 9/1992 | European Pat. Off. . |
| 0 622 462 A1 | 11/1994 | European Pat. Off. . |
| 91/00917 | 1/1991 | WIPO . |
| 92/19747 | 11/1992 | WIPO . |
| 94/00506 | 1/1994 | WIPO . |

OTHER PUBLICATIONS

Concise Encyclopedia Chemistry, (ABC Chemie (German, Translated by M. Eagleson), Jakubke & Jeschkeit (ed.), Walter de Gruyter Berlin, NY, pp. 507–508, (no month indentified 1994).

Lundgren, and R.M. Pfister, "Structure of Poly–β–hydroxybutyric Acid Grnaules", *J. Gen. Microbiol.,* vol. 34, No. 3, pp. 441–446 (no month identified 1964).

"Novel Biodegradable Microbial Polymers", E.A. Dawes, Ed., NATO ASI Series, Series E:Applied Sciences, vol. 186.

Peoples, O.P. and A.J. Sinskey, "Poly–β–hydroxybutyrate (PHB) Biosynthesis in *Alcaligenes eutrophus* H16", *The Journal of Biological Chemistry,* vol. 264, No. 26, pp. 15298–15303 (Sep. 1989).

Poirier, Y.D., D. Dennis, K. Klomparens, C. Nawarath and C. Somerville, "Perspectives on the Production of Polyhydroxyalkanoates in Plants", *FEMS Microbiology Reviews,* vol. 103, pp. 237–246 (1992).

Poirier, Y., D.E. Dennis, K. Klomparens and C. Somerville, "Polyhydroxybutyrate, a Biodegradable Thermoplastic, Produced in Transgenic Plants", *Science,* vol. 256, pp. 520–523 (Apr. 1992).

(List continued on next page.)

*Primary Examiner*—Samuel A. Acquah
*Attorney, Agent, or Firm*—Brahm J. Corstanje; Bart S. Hersko; David L. Suter

[57] ABSTRACT

The present invention relates to a process for recovering polyhydroxyalkanoate from a biological source material comprising the polyhydroxyalkanoate, the process comprising: a) comminuting the biological source material; b) air classifying the biological source material such that the polyhydroxyalkanoate particles are separated from other components of the biological source material; and c) recovering the polyhydroxyalkanoate.

28 Claims, 1 Drawing Sheet

OTHER PUBLICATIONS

Dio, Y., "Microbial Synthesis, Physcial Properties and Biodegradability of Polyhydroxyalkanoates", *Advances in Biopolymer Engineering Conference,* (Jan. 23–28, 1994).

Poole, R., In Search of the Plastic Potato, *Science,* vol. 245, pp. 1187–1189 (Sep. 1989).

Smith, E., K.A. White, D. Holt, P.A. Fentem, and S.W.J. Bright, "Expression of Polyhydroxybutyrate in Oilseed Rape", *Advanced in Biopolymer Engineering Conference,* (Jan. 23–28, 1994).

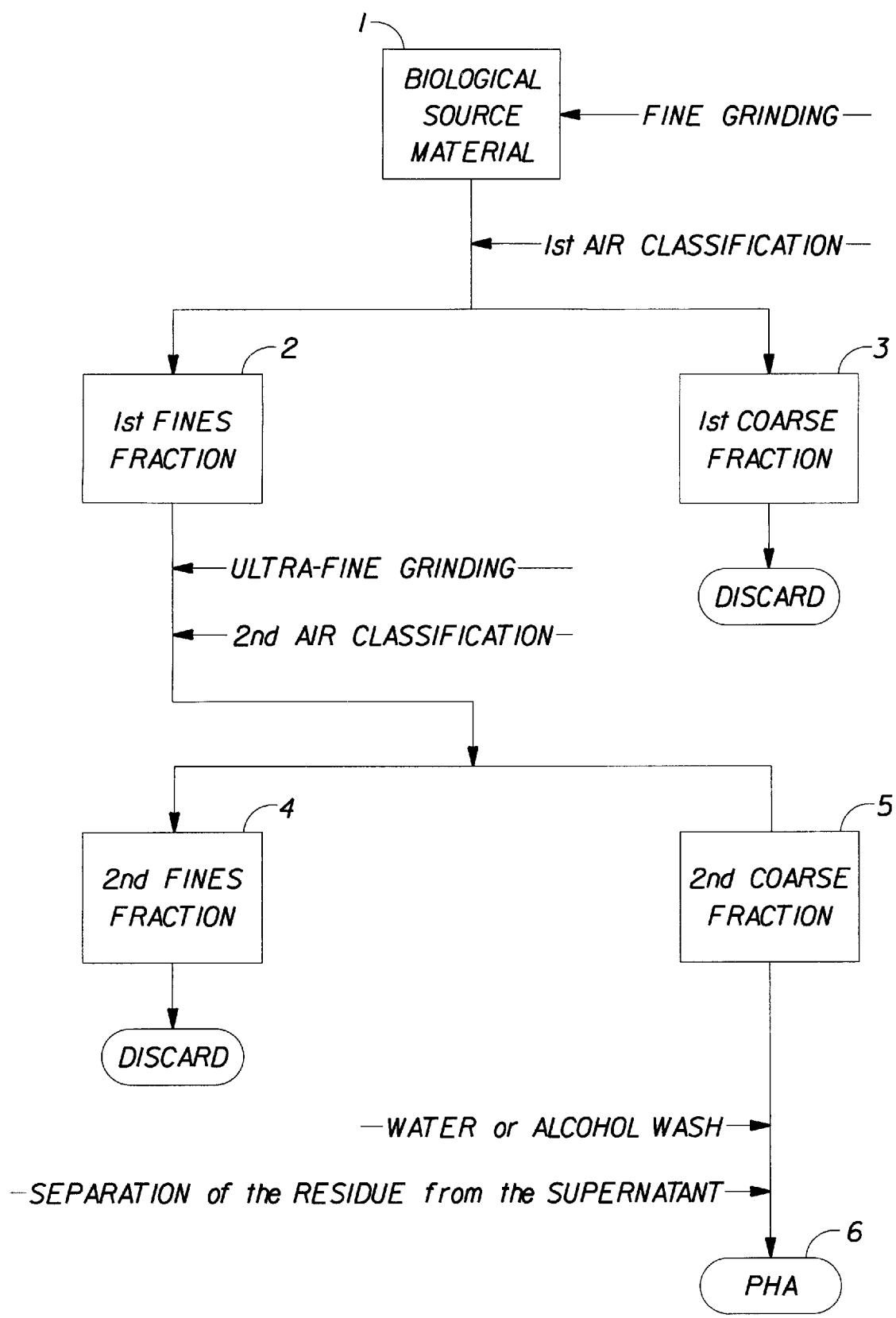

PROCESS FOR RECOVERING POLYHYDROXYALKANOTES USING AIR CLASSIFICATION

This is a continuation of application Ser. No. 08/251,829, filed on Jun. 1, 1995 now abandoned.

TECHNICAL FIELD

The present invention relates to methods of extracting specific components from other biomass components. More specifically, the present invention relates to the extraction of a polyhydroxyalkanoate from a biological system, such as a plant or bacteria, by using air classification.

BACKGROUND

Commodity polymers are typically produced from petrochemical sources by well-known synthetic means. However, recent advances in technology have resulted in the promise of new sources of commodity polymers. Particularly promising is the production of plastic resins using living organisms ("bioplastic"), including genetically manipulated bacteria and crop plants, which are designed to produce polymers such as polyhydroxyalkanoate (PHA); a number of bacteria which naturally produce PHA are also promising sources of PHA. (see for example, NOVEL BIODEGRADABLE MICROBIAL POLYMERS, E. A. Dawes, ed., NATO ASI Series, Series E: Applied Sciences—Vol. 186, Kluwer Academic Publishers (1990); Poirier, Y., D. E. Dennis, K. Klomparens and C. Somerville, "Polyhydroxybutyrate, a biodegradable thermoplastic, produced in transgenic plants", SCIENCE, Vol. 256, pp. 520–523 (1992)). In a large scale production, for example agricultural production, the harvesting and purifying of such bioplastic from the biomass debris is a critical step for determining the practical feasibility of such technology.

The separation of polymeric lipids such as PHA from a large-scale biological source, such as an agricultural crop, is not a trivial task. The conventional separation methods used extensively in the extraction of low molecular weight lipids are not practical to employ in a resin isolation process. For example, a simple mechanical press is impractical because, unlike separating vegetable oils from oil-seeds, solid plastics cannot be squeezed out of crops by mechanical pressing.

Solvent extraction is also impractical for a number of reasons. A solution of polymer develops an extremely high viscosity, even at relatively low concentration, thereby making the solution extremely difficult to work with. Furthermore, the stripping of solvent from polymer is a slow and difficult process. A commonly used solvent for the extraction of PHA from bacteria is chloroform. However, the use of a large amount of such a solvent, potentially harmful to health and environment if accidentally released, near the harvesting site would be undesirable.

Separation of PHA by sedimentational methods should be, in principle, possible. However, simple gravitational (1-G force) settling in a liquid suspending medium is, in fact, quite impractical. The rate of settling is extremely slow. In addition, such slow settling is easily disrupted by the Brownian motion of the fine PHA particles induced by the thermal fluctuation of the suspending fluid molecules surrounding the particles. Furthermore, the extended period of time required to settle very fine PHA particles introduces the problem of bacterial contamination and subsequent biodegradation of the particle suspension.

Based on the foregoing, there is a need for a simple and economical process for recovering bioplastics from a large-scale biological source. Such a process would preferably be easily adaptable as an integral part of the agricultural production of bioplastics.

It is therefore an object of the present invention to provide a process for recovering bioplastics from a biological source material.

SUMMARY

The present invention relates to a process for recovering polyhydroxyalkanoate from a biological source material comprising the polyhydroxyalkanoate, the process comprising: a) comminuting the biological source material; b) air classifying the biological source material such that the polyhydroxyalkanoate particles are separated from other components of the biological source material; and c) recovering the polyhydroxyalkanoate.

BRIEF DESCRIPTION OF THE DRAWING

FIG. 1 is a block diagram flow chart outlining an embodiment of the process of the present invention of recovering polyhydroxyalkanoate from a biological source material. In the embodiment depicted, polyhydroxyalkanoate is ultimately recovered from the second coarse fraction.

DETAILED DESCRIPTION

The present invention answers the need for a process for recovering bioplastics from a biological source material.

The following is a list of definitions for terms used herein.

"Air classification" means the separation of solid particles according to weight and/or size, by suspension in and settling from an air stream of appropriate velocity, as in air floated particulate products. Air classification may be accomplished by dropping the particles to be separated from within a tower in which such an air stream exists. Air classification may also be accomplished by using a cyclone separator. A cyclonic collector is a stationary device with no moving parts which converts the entering gas stream to a vortex. Centrifugal force acting on the particles in the gas stream causes the particles to migrate to the outside wall where they are collected by inertial impingement. (See, for example, KIRK-OTHMER ENCYCLOPEDIA OF CHEMICAL TECHNOLOGY, 3rd ed., Vol. 1, pp. 649–716).

"Comprising" means that other steps and other ingredients which do not affect the end result can be added. This term encompasses the terms "consisting of" and "consisting essentially of".

"$\mu$" means micron(s).

"Polyhydroxyalkanoate" and "PHA" mean a polymer having the following general structure:

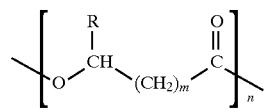

wherein R is preferably an alkyl or alkenyl, m is 1 or 2, and n is an integer. The structure enclosed in brackets is commonly referred to as a repeating unit. The terms polyhydroxyalkanoate and PHA include polymers containing one or more different repeating units. Examples of preferred PHAs recoverable by the present process included those disclosed in U.S. patent application Ser. No. 08/187,969, Noda, filed Jan. 28, 1994; U.S. patent application Ser. No. 08/188,271, Noda, filed Jan. 28, 1994; U.S. patent application Ser. No. 08/189,029, Noda, filed Jan. 28, 1994; and European Patent Application Ser. No. 533 144, Shiotani and Kobayashi, published Mar. 24, 1993.

"Recovering polyhydroxyalkanoate from a biological source material", in addition to referring to the recovery of the partilcular PHA produced by a biological source material which produces a single PHA, also refers to the recovery of one or more types of PHA when the biological source material produces more than one type of PHA.

"Alkyl" means a carbon-containing chain which may be straight, branched or cyclic, preferably straight; substituted (mono- or poly-) or unsubstituted; and saturated.

"Alkenyl" means a carbon-containing chain which may be straight, branched or cyclic, preferably straight; substituted (mono- or poly-) or unsubstituted; and monounsaturated (i.e., one double or triple bond in the chain), or polyunsaturated (i.e., two or more double bonds in the chain, two or more triple bonds in the chain, or one or more double and one or more triple bonds in the chain).

The present invention relates to a process for recovering (i.e., isolating) polyhydroxyalkanoate from a biological source material comprising the polyhydroxyalkanoate, the process comprising: a) comminuting the biological source material; b) air classifying the biological source material such that the polyhydroxyalkanoate particles are separated from other components of the biological source material; and c) recovering the polyhydroxyalkanoate.

Biological Source Material

Sources from which PHA is recovered via the process of the present invention include single-cell organisms such as bacteria or fungi and higher organisms such as plants (herein collectively referred to as "biological source material" or "BSM"). While such BSM could be wild-type organisms, they are preferably genetically manipulated species specifically designed for the production of a specific PHA of interest to the grower. Such genetically manipulated organisms are produced by incorporating the genetic information necessary to produce one or more types of PHA. Typically, such genetic information is derived from bacteria which naturally produce PHA.

Plants useful in the present invention include any genetically engineered plant designed to produce PHA. Preferred plants include agricultural crops such cereal grains, oil seeds and tuber plants; more preferably, avocado, barley, beets, broad bean, buckwheat, carrot, coconut, copra, corn (maize), cottonseed, gourd, lentils, lima bean, millet, mung bean, oat, oilpalm, peas, peanut, potato, pumpkin, rapeseed (e.g., canola), rice, sorghum, soybean, sugarbeet, sugar cane, sunflower, sweetpotato, tobacco, wheat, and yam. Such genetically altered fruit-bearing plants useful in the process of the present invention include, but are not limited to, apple, apricot, banana, cantaloupe, cherries, grapes, kumquat, lemon, lime, orange, papaya, peaches, pear, pineapple, tangerines, tomato, and watermelon. Preferably the plants are genetically engineered to produced PHA pursuant to the methods disclosed in Poirier, Y., D. E. Dennis, K. Klomparens and C. Somerville, "Polyhydroxybutyrate, a biodegradable thermoplastic, produced in transgenic plants", SCIENCE, Vol. 256, pp. 520–523 World Patent Application Publication No. 95/05472, published Feb. 23, 1995; and World Patent Application Publication No. 93/02187, published Feb. 4, 1993. Particularly preferred plants are soybean, potato, corn and coconut plants genetically engineered to produce PHA.

Bacteria useful in the present invention include any genetically engineered bacteria designed to produce PHA, as well as bacteria which naturally produce PHA. Examples of such bacteria include those disclosed in NOVEL BIODEGRADABLE MICROBIAL POLYMERS, E. A. Dawes, ed., NATO ASI Series, Series E: Applied Sciences—Vol. 186, Kluwer Academic Publishers (1990); U.S. Pat. No. 5,250,430, Peoples and Sinskey, issued Oct. 5, 1993; U.S. Pat. No. 5,245,023, Peoples and Sinskey, issued Sep. 14, 1993; U.S. Pat. No. 5,229,279, Peoples and Sinskey, issued Jul. 20, 1993.

It is preferable that the BSM contain a sufficient quantity of PHA to make the process economically desirable. Preferably, the initial content of PHA in the source material should be at least about 5% of the total dry weight; more preferably at least about 25%; more preferably at least about 50%; more preferably still, at least about 75%.

Isolation Process

The size of the PHA particles found in the BSM will vary, depending upon a variety of factors, including the type of BSM and the organelle in which the PHA is stored in the BSM. As a result, the air-classification fraction (fines or coarse) in which the PHA is ultimately recovered from will vary depending upon the size of the PHA particles relative to the particle size of the other BSM components.

The process of the present invention yields at least about 70% of the PHA in the source material, more preferably at least about 80%, more preferably still at least about 90%.

Preferably, at least about 85% of the dry mass of the PHA-rich fraction ultimately recovered by the process of the present invention is PHA, more preferably at least about 95%, more preferably still at least about 99%.

A. Recovery of PHA from the Fines Fraction

PHA is typically produced in the BSM as particles having a diameter of about 1 $\mu$. At 1 $\mu$, the PHA particles are typically one of the smallest size components of the BSM, particularly in comparison to the protein and carbohydrate particles.

In one embodiment of the present invention, the BSM is finely ground, for example in a pin mill, so that at least about 90% of the particles are at least less than about 100 $\mu$ in diameter, such as in a pin mill. The comminuted BSM is then air classified to produce a fines fraction, containing the finer particles in the comminuted BSM (preferably at least about 90% are about 1 $\mu$ in diameter), and a coarse fraction, containing the larger particles in the BSM. Air classifiers useful in the present invention preferably involve feeding the particles into a rotor by means of mixing them with an air stream which flows directly through the rotor. The centrifugal force supplied by the rotor moves the coarse particles to the wall of the rotor. The fine particles go through the rotor with the air stream because they have a smaller mass to size ratio. The air flow rate and the rotor speed are important variables which vary depending upon the material being separated and the air classifier being used. Generally, the fines fractions will be higher in PHA concentration. The fine grinding and air classification may be accomplished by any convenient method. For example, Pfeiffer, V. F., A. C. Stringfellows, and E. L. Griffin, Jr., "Fractionating Corn, Sorghum and Soy Flours by Fine Grinding and Air Classification", AMERICAN MILLER AND PROCESSOR, August 1960, pp. 11–13, 24, discloses one known method for carrying out fine grinding and air classification. At this point the fines fraction may then be washed in water, or in a 20 to 80% by weight aqueous alcohol solution of methanol, ethanol or isopropanol. The solvent to BSM ratio is preferably from about 4:1 to about 20:1. The solid PHA-containing concentrate can be separated from the liquid supernatant by filtration, centrifugation, or any other convenient method.

B. Recovery of PHA from the "Second Coarse Fraction"

In another embodiment of the present invention, particularly where PHA particles occurring in the BSM are not necessarily the smallest size particle, the PHA particles may be recovered by the following process: Referring to FIG. 1, the BSM (1) is finely ground so that at least about 90% of the particles are at least less than about 100 $\mu$ in diameter. Then, the comminuted BSM is subjected to the first air classification step to produce a first fines fraction of from about 60 to about 90% by weight (2) and a first coarse fraction (3) which is discarded or recycled. The 60 to 90% range allows a preferred balance between yield and high PHA concentration. As the desired PHA concentration is increased, the amount of concentrate that can be obtained decreases.

The first fines fraction (2) from above is then ultra finely ground, preferably in a fluid energy mill, so that at least about 90% of the particles are less than about 20 $\mu$ in diameter. A vibration energy mill or other suitable apparatus may also be used. A larger size limitation will now allow a good separation in the following air classification step.

The ultra-finely ground BSM is then subjected to a second air classification step. A second coarse fraction (5) of from about 50 to about 90% by weight is removed. The second fines fraction (4) is discarded or recycled. The 50 to 90% range is preferred because it allows for a preferred balance between yield and high PHA concentration. The second coarse fraction (5), which is the ultimate product of the two air classification steps, should constitute about 30 to about 80% by weight of the original starting BSM, more preferably from about 40 to about 60%. If the two air classification steps are carried out at the above-described conditions, the ultimate product will preferably fall within the 30 to 80% range. Again, this range provides a preferred balance between yield and high concentration. If higher yields are obtained, the PHA level is reduced. It is possible to obtain very high PHA concentrations, but the small yield makes it uneconomical to do so.

The second coarse fraction (5) is then washed in water, or in a 20 to 80% by weight aqueous alcohol solution of methanol, ethanol or isopropanol. The solvent to BSM ratio is preferably from about 4:1 to about 20:1. The solid PHA-containing concentrate (6) can be separated from the liquid supernatant by filtration, centrifugation, or any other convenient method.

This process produces a PHA concentrate which contains at least about 70% PHA, more preferably at least about 80% PHA, more preferably at least about 85% PHA, more preferably at least about 90% PHA, more preferably still at least about 90% PHA.

To obtain a PHA concentrate with even less undesirable material, the first fines fraction is air classified again; this time, a second coarse fraction containing the PHA is taken off. The second fines fraction will contain some of the finer undesirable materials. More preferably, the fines fraction from the first air classification step, the first fines fraction (2), is ultra-finely ground and then air classified again. The PHA is contained in the coarse fraction of this second air classification, i.e., the second coarse fraction (5). Without being bound by theory, it is believed that the undesirable materials left in the first fines fraction after the first air classification step, which normally are not separated from the PHA during this step, are separated from the PHA during the second air classification step when the first fines fraction is ground to an ultra-fine particle size before it is air classified the second time.

C. Controlling the Fraction (Fines or Coarse) in Which PHA is Recovered From Other embodiments of the present invention include manipulation of the relative BSM component particle sizes via varying levels of grinding prior to the air classification (s). Such size manipulation is facilitated by the fact that PHA does not absorb water, whereas components such as proteins and carbohydrates do. If, prior to air classification, it is desirable to have the PHA particles smaller than the other BSM components, then the BSM is hydrated with water. Following hydration, the BSM is subjected to grinding. The hydrated components will be more difficult to grind into very small particles, whereas the PHA (which has not been hydrated) will be easily ground into very small particles. In such a procedure, the majority of the PHA particles would occur in the fines fraction.

Alternatively, the BSM can be dehydrated. In this state, the other components are capable of being finely ground into particles much smaller than the PHA. In this procedure, the majority of the PHA particles would occur in the coarse fraction.

All percentages are by weight of total composition unless specifically stated otherwise.

The PHAs recovered by the process of this invention are useful for forming a variety of plastic articles, including those disclosed in U.S. patent application Ser. No. 08/187,969, Noda, filed Jan. 28, 1994; U.S. patent application Ser. No. 08/188,271, Noda, filed Jan. 28, 1994; and U.S. patent application Ser. No. 08/189,029, Noda, filed Jan. 28, 1994. Such plastic articles include, but are not limited to, films, sheets, foams, fibers, nonwovens, elastomers, adhesive and molded articles. Such plastic articles can be further incorporated into a variety of useful products including, but not limited to, personal cleansing wipes; disposable health care products such as bandages, wound dressings, wound cleansing pads, surgical gowns, surgical covers, surgical pads; other institutional and health care disposables such as gowns, wipes, pads, bedding items such as sheets and pillowcases, foam mattress pads.

The following non-limiting examples illustrate the methods of the present invention.

EXAMPLE 1

Isolation of Poly(3-hydroxybutyrate-co-3-hydroxyoctanoate) from Maize

Grains of maize (corn), from a genetically altered maize plant, comprising poly(3-hydroxybutyrate-co-3-hydroxyoctanoate) are hammer milled to form meal. The low molecular weight lipids and oils contained in the meal are removed first by pressing the flakes and then further extracted by using hexane as the solvent. The meal is then washed with 40% water/60% ethanol mixture to remove other soluble components such as sugars. The resulting defatted and desugared meals are then finely pulverized using a fluid energy mill (Fluid Energy Aljet, Plumsteadville, Pa.) at a feed rate of 100 grams/min, such that 90% of the particles are less than 10 $\mu$ in diameter and 40% are less than about 2 $\mu$ in diameter. This milled sample is air classified using an air classifier (Alpine 100 MZR, Summit, N.J.) to produce a 46% fines fraction, and a 54% coarse fraction in which 9% of the particles are less than 15 $\mu$ in diameter and no more than about 10% are less than 2 $\mu$ in diameter. The air flow rate is 37 cubic meters per hour and the rotor speed is 13,000 revolutions per minute. The fines fraction is then subjected to chloroform extraction followed by methanol precipitation to produce poly(3- hydroxybutyrate-co-3-hydroxyoctanoate) particles having a purity of about 85% or higher, and a yield of about 80% or higher with respect to the starting material.

EXAMPLE 2

Isolation of Poly(3-hydroxybutyrate-co-3-hydroxyhexanoate) from Tobacco

Dried leaves from a genetically altered tobacco plant, comprising poly(3-hydroxybutyrate-co-3-hydroxyhexanoate) are finely ground so that 90% of the particles are less than 60 $\mu$ in diameter using a grinding mill (Alpine Kolloplex 160 mill, Summit, N.J.). The low molecular weight components contained in the leaves are removed prior to the grinding by using hexane as the solvent and washed with 40% water/60% ethanol mixture to remove other soluble components. After milling, the tobacco leaf flour is air classified using an laboratory air classifier (Alpine 100 MZR, Summit, N.J.) to yield a 75% first fines fraction in which 90% of the particles are less than 40 $\mu$ in diameter, and a 25.6% first coarse fraction. The air flow rate is 45.25 cubic meters per hour and the rotor speed is 4,750 revolutions per minute. The first fines fraction is milled such that 90% of the particles are less than about 15 $\mu$ in diameter and 40% are less than 4 $\mu$ in diameter using a fluid energy mill (Fluid Energy Aljet, Plumsteadville, Pa.) at a feed rate of 100 grams/min. This milled sample is again air classified to yield a 46% second fines fraction, and a 54% second coarse fraction in which 9% of the particles are less than 15 $\mu$ in diameter and no more than about 10% are less than 4 $\mu$ in diameter. The air flow rate is 37 cubic meters per hour and the rotor speed is 13,000 revolutions per minute. Each of these fractions (first coarse, second coarse, and second fines fractions) are then washed at room temperature for 1 hour with water using a 10:1 water:tobacco leaf flour ratio. The mixture is centrifuged and the recovered residue is rewashed in the same way using a 5:1 water:tobacco leaf flour ratio. The residue is again recovered by centrifugation and is then freeze-dried. Poly(3-hydroxybutyrate-co-3-hydroxyhexanoate) is recovered from each of the fractions by chloroform extraction followed by methanol precipitation.

EXAMPLE 3

Isolation of Poly(3-hydroxybutyrate-co-3-hydroxyvalerate) from Soybeans

Grains from a genetically altered soybean plant, comprising poly(3-hydroxybutyrate-co-3-hydroxyvalerate) are hammer milled to form meal. The low molecular weight lipids and oils contained in the meals are removed first by pressing the flakes and then further extracted by using hexane as the solvent. The meal is then washed with 40% water/60% ethanol mixture to remove other soluble components such as sugars. The resulting defatted and desugared meal is partially hydrated to the moisture level of 15% by mixing with a predetermined amount of water in a sealed container at 65° C. for three hours. The meal is then finely pulverized using a fluid energy mill (Fluid Energy Aljet, Plumsteadville, Pa.) at a feed rate of 100 grams/min, such that 60% of the particles are less than 100 $\mu$ in diameter and 30% are less than 30 $\mu$ in diameter. The milled sample is subsequently air classified using an air classifier (Alpine 100 MZR, N.J.) to produce a 26% fines fraction, and a 74% coarse fraction in which 19% of the particles are more than 150 $\mu$ in diameter and no more than about 10% are more than 300 $\mu$ in diameter. The air flow rate is 38 cubic meters per hour and the rotor speed is 13,000 revolutions per minute. The fines fraction is then subjected to chloroform extraction followed by methanol precipitation to produce poly(3-hydroxybutyrate-co-3-hydroxyvalerate) particles having a purity of about 85% or higher, and a yield of about 80% or higher with respect to the starting material.

EXAMPLE 4

Isolation of Poly(3-hydroxybutyrate-co-3-hydroxydecanoate) from Coconuts

Coconut seeds from a genetically altered coco palm plant, comprising poly(3-hydroxybutyrate-co-3-hydroxydecanoate) are shredded to form thin flakes. The low molecular weight oils contained in the coco meal are removed first by using hexane as the solvent and washed with 40% water/60% ethanol mixture to remove other soluble components such as sugars. The resulting defatted and desugared flakes are thoroughly dried to the moisture level of less than 1.5% by a low-pressure oven for sixteen hours. The flakes are then finely pulverized using a fluid energy mill (Fluid Energy Aljet, Plumsteadville, Pa.) at a feed rate of 100 grams/min, such that 30% of the particles are less than 15 $\mu$ in diameter and no more than about 10% are less than 5 $\mu$ in diameter. The milled sample is subsequently air classified using an air classifier (Alpine 100 MZR, Summit, N.J.) to produce a 38% fine fraction and a 62% coarse fraction. The air flow rate is 32 cubic meters per hour and the rotor speed is 14,000 revolutions per minute. The coarse fraction is then subjected to chloroform extraction followed by methanol precipitation to produce poly(3-hydroxybutyrate-co-3-hydroxydecanoate) particles having a purity of about 95% or higher, and a yield of about 85% or higher with respect to the starting material.

EXAMPLE 5

Isolation of Poly(3-hydroxybutyrate) from *A. eutrophus*

A culture of *Alcaligenes eutrophus* which naturally produces poly(3-hydroxybutyrate) is treated with an ultrasonic sonicator (Branson Ultrasonic Corp., Dandury, Conn.) to produce a suspension mixture consisting of fine granules poly(3-hydroxybutyrate) having an average particle size of less than 1 $\mu$ and other bacterial biomass debris containing about 20% solids by weight. The suspension is then freeze dried and subsequently pulverized using a fluid energy mill (Fluid Energy Aljet, Plumsteadville, Pa.) at a feed rate of 100 grams/min, such that 90% of the particles are less than 5 $\mu$ in diameter. The milled sample is subsequently air classified using an air classifier (Alpine 100 MZR, Summit, N.J.). The air flow rate is 34 cubic meters per hour and the rotor speed is 12,000 revolutions per minute. The fines fraction is then subjected to chloroform extraction followed by methanol precipitation to produce poly(3-hydroxybutyrate) particles having a purity of about 95% or higher, and a yield of about 85% or higher with respect to the starting material.

EXAMPLE 6

Isolation of Poly(3-hydroxybutyrate-co-3-hydroxyheptanoate) from *E. coli*

A culture of *E. coli* which has been genetically manipulated to produces poly(3-hydroxybutyrate-co-3-hydroxyheptanoate) is treated with an ultrasonic sonicator (Branson Ultrasonic Corp., Dandury,Conn.) to produce a suspension mixture consisting of fine granules of poly(3-hydroxybutyrateco-3-hydroxyheptanoate) having an average particle size of 2 μ and other bacterial biomass debris containing about 5% solids by weight. The suspension is then freeze dried and subsequently pulverized using a fluid energy mill (Fluid Energy Aljet, Plumsteadville, Pa.) at a feed rate of 100 grams/min, such that 90% of the particles are less than 5 μ in diameter. The milled sample is air classified using an air classifier (Alpine 100 MZR, Summit, N.J.). The air flow rate is 34 cubic meters per hour and the rotor speed is 12,000 revolutions per minute. The fines fraction is then subjected to chloroform extraction followed by methanol precipitation to produce poly(3-hydroxybutyrate-co-3-hydroxyheptanoate) particles having a purity of about 97% or higher, and a yield of about 90% or higher with respect to the starting material.

All publications and patent applications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A process for recovering polyhydroxyalkanoate from a biological source material comprising the polyhydroxyalkanoate, the process comprising:
   a. comminuting the biological source material;
   b. air classifying the biological source material whereby the polyhydroxyalkanoate particles are separated from other components of the biological source material; and
   c. recovering the polyhydroxyalkanoate.

2. The process of claim 1, wherein the biological source material is plant material.

3. The process of claim 2, wherein the biological source material is avocado, barley, beets, broad bean, buckwheat, carrot, coconut, copra, corn, cottonseed, gourd, lentils, lima bean, millet, mung bean, oat, oilpalm, peas, peanut, potato, pumpkin, rapeseed, rice, sorghum, soybean, sugarbeet, sugar cane, sunflower, sweetpotato, tobacco, wheat, yam, apple, apricot, banana, cantaloupe, cherries, grapes, kumquat, lemon, lime, orange, papaya, peaches, pear, pineapple, tangerines, tomato, or watermelon.

4. The process of claim 3, wherein the biological source material is soybean.

5. The process of claim 3, wherein the biological source material is corn.

6. The process of claim 3, wherein the biological source material is potato.

7. The process of claim 1, wherein the biological source material is bacteria.

8. A process for recovering polyhydroxyalkanoate from a biological source material comprising the polyhydroxyalkanoate, the process comprising:
   a. fine grinding the biological source material whereby the other components of the biological source material become no less than about 10 μ in diameter;
   b. air classifying the biological source material from step (a) to produce a fines fraction and a coarse fraction and removing the coarse fraction;
   c. washing the fines fraction with a solution of water or a 20 to 80% by weight aqueous alcoholic solution, and separating a polyhydroxyalkanoate-containing residue from the liquid supernatant.

9. The process of claim 8, wherein the polyhydroxyalkanoate occurs in the biological source material as particles having a diameter of about 1 μ.

10. The process of claim 8, wherein the biological source material is plant material.

11. The process of claim 10, wherein the biological source material is avocado, barley, beets, broad bean, buckwheat, carrot, coconut, copra, corn, cottonseed, gourd, lentils, lima bean, millet, mung bean, oat, oilpalm, peas, peanut, potato, pumpkin, rapeseed, rice, sorghum, soybean, sugarbeet, sugar cane, sunflower, sweetpotato, tobacco, wheat, yam, apple, apricot, banana, cantaloupe, cherries, grapes, kumquat, lemon, lime, orange, papaya, peaches, pear, pineapple, tangerines, tomato, or watermelon.

12. The process of claim 11, wherein the biological source material is soybean.

13. The process of claim 11, wherein the biological source material is corn.

14. The process of claim 11, wherein the biological source material is potato.

15. The process of claim 8, wherein the biological source material is bacteria.

16. A process for recovering polyhydroxyalkanoate from a biological source material comprising the polyhydroxyalkanoate, the process comprising:
   a. fine grinding the biological source material whereby at least about 90% of the particles become less than about 100 μ in diameter;
   b. air classifying the biological source material from step (a) to produce a first fines fraction and a first coarse fraction and removing the first fines fraction which is from about 60 to about 90% by weight of the of the ground biological source material and wherein at least about 90% of the first fines fraction particles are less than about 45 μ in diameter;
   c. ultra-finely grinding the first fines fraction from step (b) whereby at least about 90% of the particles become less than 20 μ in diameter;
   d. air classifying the ground first fines fraction from step (c) to produce a second fines fraction and a second coarse fraction and removing the second coarse fraction which is from about 50 to about 90% by weight of the ground first fines fraction and wherein at least about 80% of the second coarse fraction particles are less than about 20 μ in diameter; and
   e. washing the second coarse fraction with a solution consisting of water at a pH of from about 4 to about 6 or a 20 to 80% by weight aqueous alcoholic solution, and separating a polyhydroxyalkanoate-containing residue from the liquid supernatant.

17. The process of claim 16, wherein a fluid energy mill is used in step (c).

18. The process of claim 17, wherein step (e) comprises washing the coarse fraction from step (d) in a 20 to 80% by weight aqueous alcohol solution of methanol, ethanol or isopropanol solution.

19. The process of claim 16, wherein step (a) comprises pin milling the biological source material whereby at least about 90% of the particles become less than 100 μ in diameter.

20. The process of claim 16, wherein the biological source material is plant material.

21. The process of claim 20, wherein the biological source material is avocado, barley, beets, broad bean, buckwheat, carrot, coconut, copra, corn, cottonseed, gourd, lentils, lima bean, millet, mung bean, oat, oilpalm, peas, peanut, potato, pumpkin, rapeseed, rice, sorghum, soybean, sugarbeet, sugar cane, sunflower, sweetpotato, tobacco, wheat, yam, apple, apricot, banana, cantaloupe, cherries, grapes, kumquat, lemon, lime, orange, papaya, peaches, pear, pineapple, tangerines, tomato, or watermelon.

22. The process of claim 21, wherein the biological source material is soybean.

23. The process of claim 21, wherein the biological source material is corn.

24. The process of claim 21, wherein the biological source material is potato.

25. The process of claim 16, wherein the biological source material is bacteria.

26. The polyhydroxyalkanoate recovered by the process of claim 1.

27. The polyhydroxyalkanoate recovered by the process of claim 8.

28. The polyhydroxyalkanoate recovered by the process of claim 16.

\* \* \* \* \*